United States Patent [19]

Hartman et al.

[11] Patent Number: 4,894,390
[45] Date of Patent: * Jan. 16, 1990

[54] SUBSTITUTED THIENO[2,3-B]THIOPHENE-2-SULFONAMIDES AS ANTIGLAUCOMA AGENTS

[75] Inventors: George D. Hartman, Lansdale; John D. Prugh, Chalfont, both of Pa.

[73] Assignee: Merck & Co., Inc., Rahway, N.J.

[*] Notice: The portion of the term of this patent subsequent to Feb. 21, 2006 has been disclaimed.

[21] Appl. No.: 260,632

[22] Filed: Oct. 21, 1988

Related U.S. Application Data

[63] Continuation-in-part of Ser. No. 191,085, May 4, 1988, which is a continuation-in-part of Ser. No. 162,532, Mar. 1, 1988, abandoned, and a continuation-in-part of Ser. No. 80,851, Aug. 3, 1987, abandoned.

[51] Int. Cl.$^4$ ............... A61K 31/38; C07D 333/32
[52] U.S. Cl. ............................. 514/443; 549/50
[58] Field of Search ...................... 549/50; 514/443

[56] References Cited

U.S. PATENT DOCUMENTS

| | | | |
|---|---|---|---|
| 3,733,322 | 5/1973 | Wright | 549/50 |
| 4,665,090 | 5/1987 | Graham | 514/445 |
| 4,668,697 | 5/1987 | Shepard et al. | 514/443 |

FOREIGN PATENT DOCUMENTS

| | | |
|---|---|---|
| 0129478 | 6/1984 | European Pat. Off. |
| 0228237 | 12/1986 | European Pat. Off. |
| 2378783 | 9/1978 | France .............. 514/443 |

OTHER PUBLICATIONS

Kvitko et al. J. Org. Chem. 12, 1550 (1976).

*Primary Examiner*—Alan Siegel
*Attorney, Agent, or Firm*—William H. Nicholson; Joseph F. Di Prima

[57] ABSTRACT

Aromatic sulfonamides useful in the treatment of elevated intraocular pressure having the structural formula:

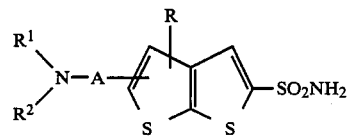

wherein A, R, $R^1$, and $R^2$ are as hereinafter defined, as well as the pharmaceutically and ophthalmologically acceptable salts thereof.

3 Claims, No Drawings

SUBSTITUTED THIENO[2,3-B]THIOPHENE-2-SULFONAMIDES AS ANTIGLAUCOMA AGENTS

SUMMARY OF THE INVENTION

This is a continuation-in-part of copending application Ser. No. 191,085 filed May 4, 1988, which in turn is a continuation-in-part of copending application Ser. No. 162532 filed Mar. 1, 1988, now abandoned, which in turn is a continuation-in-part of copending application Ser. No. 080851, filed Aug. 3, 1987, now abandoned.

This invention relates to novel aromatic sulfonamides useful in the treatment of elevated intraocular pressure. More particularly this invention relates to compounds having the structural formula:

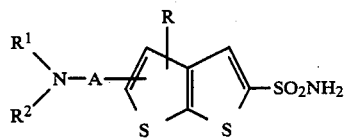

wherein A, R, $R^1$, and $R^2$ are as hereinafter defined, as well as the pharmaceutically and opthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma. The invention also relates to processes for preparation of the novel compounds.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2-5-thiadiazol-3-yl)oxyl]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

DETAILED DESCRIPTION OF THE INVENTION

The novel compounds of this invention have structural formula:

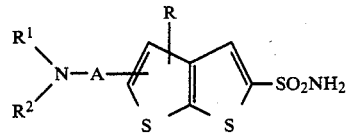

or a pharmaceutically acceptable salt thereof, wherein
A is $C_{1-8}$ alkylene, either straight or branched chain and either unsubstituted or substituted with $C_{1-3}$ alkoxy or hydroxy;
R is hydrogen or $C_{1-6}$ alkyl, either straight or branched chain; and
$R^1$ and $R^2$ are independently:
  (1) hydrogen,
  (2) $C_{1-6}$ alkyl, either unsubstituted or substituted with one or more of
    (a) $C_{3-6}$ cycloalkyl,
    (b) $C_{1-3}$ alkoxy,
    (c) $C_{1-3}$ alkoxy-$(C_{2-4}$ alkoxy$)_n$—, wherein n is 1-6
    (d) hydroxy,
    (e) halo, such as chloro, bromo or fluoro,
    (f) $C_{1-3}$ alkyl—$S(O)_n$—, wherein n is 0-2
    (g) phenyl, or
    (h) —$NR^3R^4$ wherein $R^3$ and $R^4$ are independently selected from
      (i) hydrogen and
      (ii) $C_{1-6}$ alkyl, either unsubstituted or substituted with one or more of $C_{1-3}$ alkoxy, hydroxy or phenyl;

wherein $R^5$ is $C_{1-4}$ alkyl either straight or branched chain and either unsubstituted or substituted with one or more of $C_{1-3}$ alkoxy, or hydroxy; or
(4) taken together with the nitrogen atom to which they are attached form a 5 to 7-membered heterocycle such as piperidine, morpholine, piperazine, N—$C_{1-3}$ alkylpiperazine, or thiomorpholine, thiomorpholine-S-oxide, or thiomorpholine-S,S-dioxide.

A preferred embodiment of the novel compounds is that wherein A is joined to the 5-position of the thieno[2,3-b]thiophene ring system.

It is still more preferred that A is —(CH$_2$)—$_{1-3}$, especially —CH$_2$—.

It is also preferred that R$^1$ and R$^2$ are independently $C_{1-3}$alkoxyethyl or $C_{1-3}$alkoxy—$C_{2-4}$alkoxy-ethyl.

The novel processes for preparing the novel compounds of this invention are illustrated as follows, wherein Ar represents

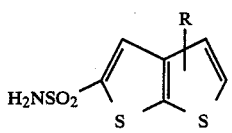

and A' represents $C_{0-7}$alkylene either unsubstituted or substituted with $C_{1-3}$alkoxy or hydroxy;

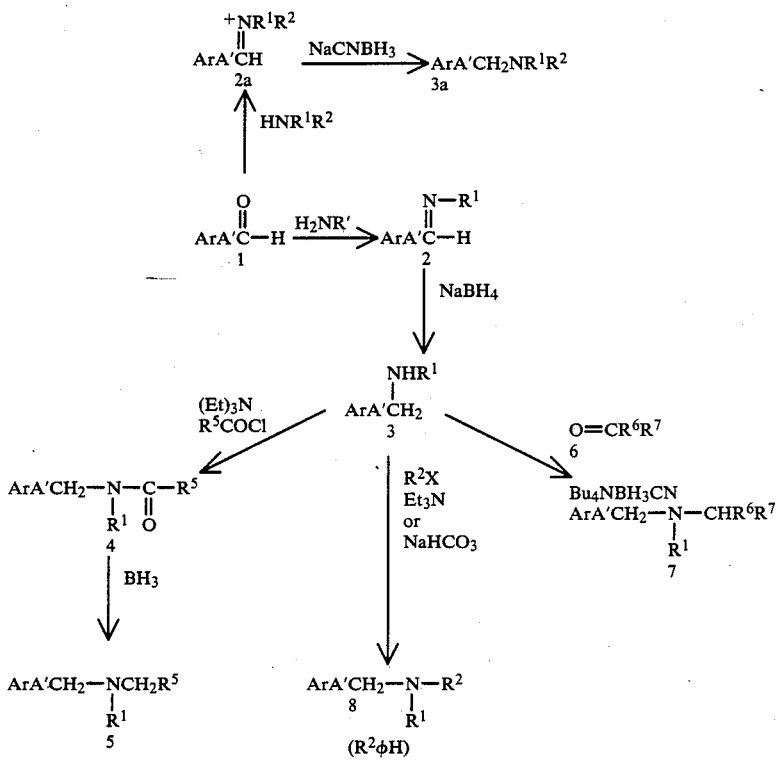

The process comprises treating the aldehyde, 1, in the presence of an acid such as HCl gas with the amine H$_2$NR$^1$ or HNR$^1$R$^2$ at about 15° to 60° C. in a $C_{1-3}$ lower alkanol solvent such as methanol or ethanol for about 0.5 to 72 hours. The crystalline precipitate 2 or 2a is treated with a complex metal hydride such as sodium borohydride in the case of 2 or sodium cyanoborohydride in the case of 2a at about 0° to 20° C. and continuing stirring for about 0.5 to 72 hours. Alternatively, the crystalline precipitate (2 or 2a) may be isolated by filtration and resuspended prior to treatment with the hydride.

Compound 3 is converted into a tertiary amine either by acylation to 4 and reduction to 5, or by treatment with ketone 6, followed by reduction to give 7. Conversion of 3 to 4 would be carried out in an aprotic solvent such as ether, THF, or the like in the presence of a base such as triethylamine at about room temperature, and the subsequent reduction to 5 by BH$_3$·S(CH$_3$)$_2$ would be carried out at about room temperature in a solvent such as toluene, CH$_2$Cl$_2$ of THF.

Conversion of 3 to 7 would be carried out by treatment of 3 with an equivalent amount of ketone 6 at about room temperature in a solvent such as a halocarbon (methylene chloride) or an alcohol such as methanol.

Alternatively, secondary amine 3 can be converted to tertiary amine 8 simply by alkylation. Thus, treatment of 3 in ether, THF, DMF or halocarbon solution with an alkyl halide, RX, (iodide, bromide or chloride) in the presence of an organic (i—C$_3$H$_2$)$_2$N(C$_2$H$_5$) or inorganic (NaHCO$_3$) base would give 8.

Those novel compounds wherein A is branched chain alkylene can be prepared either from the aldehyde as shown in the above reaction schemes wherein A' is a branched chain alkylene, or from the aromatic aldehyde as shown below:

-continued

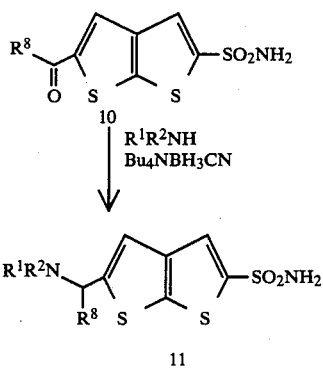

In this process 9 is treated with excess organolithium reagent $R^8Li$ in ether or THF at $-78°$ to $-30°$. This is quenched with $H_2O$ and the product extracted. This alcohol is oxidized to ketone 10 with pyridinium chlorochromate (PCC) in $CH_2Cl_2$/tetrahydrofuran at room temperature (2-3 hours). The ketone 10 is reductively aminated with amine $R^1R^2NH/Bu_4NBH_3CN$ in an alcohol ($CH_3OH$) at room temperature for 1 hour to 10 days to provide 11. In this manner the following compounds are made:

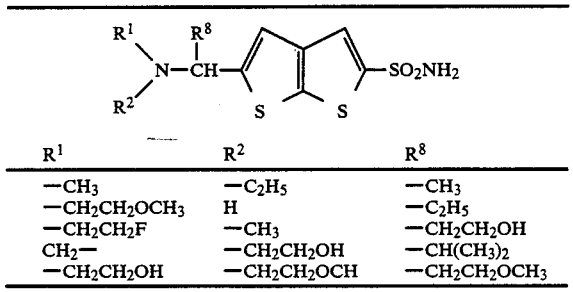

| $R^1$ | $R^2$ | $R^8$ |
|---|---|---|
| —$CH_3$ | —$C_2H_5$ | —$CH_3$ |
| —$CH_2CH_2OCH_3$ | H | —$C_2H_5$ |
| —$CH_2CH_2F$ | —$CH_3$ | —$CH_2CH_2OH$ |
| $CH_2$— | —$CH_2CH_2OH$ | —$CH(CH_3)_2$ |
| —$CH_2CH_2OH$ | —$CH_2CH_2OCH$ | —$CH_2CH_2OCH_3$ |

The novel pharmaceutical formulations of this invention are adapted for topical ocular administration in the form of solutions, ointments, solid water soluble polymeric inserts, or solutions which get at body temperature or in the presence of lachrymal fluids for the treatment of glaucoma and other stages of elevated intraocular pressure and contain about 0.1% to 15% by weight of medicament, especially about 0.5% to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations each of the active agents is present in an amount approximating that found in its single entity formulations.

The novel method of treatment of this invention comprises the treatment of elevated intraocular pressure by the administration of an effective amount of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

5-Isobutylaminomethylthieno[2,3-b]thiophene-2-sulfonamide hydrochloride

Step A: Preparation of Methyl [3-(2-dioxolanyl)-thiophene-2-ylthio]acetate

Thiophene-2-carboxaldehyde ethylene acetal (15.62 g, 0.1 mol) was dissolved in dry THF (200 ml) in an inert atmosphere and cooled to $-74°$ C. n-Butyl lithium (44 mL of a 2.3M solution in hexane; 0.1 mol) was added at a rapid drip rate over 20 minutes (the temperature rose to $-68°$ C.). After the addition was complete, the mixture was stirred at $-60°$ C. to $-74°$ C. for 35 minutes. After about 5 minutes, the lithium derivative began to crystallize. Most crystallized after 35 minutes. Sulfur (as a fine powder; 3.21 g, 0.1 mol) in 1 g and 2.21 g portions was added 5 minutes apart (temperature rose from $-74°$ to $-65°$ C.). The reaction was stirred at $-74°$ C. for 15 minutes and slowly warmed with stirring to $-50°$ C. where it was held for 15 minutes then warmed to $-38°$ C. over 15 minutes. Methyl bromoacetate (9.9 mL, 16.1 g, 0.105 mol) was added at a slow drip rate over a period of 8 minutes (temperature rose from $-40°$ C. to $-25°$ C.) and the reaction mixture was allowed to stir at ambient temperature until the temperature rose to $0°$ C. After warming to $24°$ C. the reaction mixture was stirred at room temperature for 2 hours. The reaction was worked up by evaporating the solvent in vacuo and partitioning the residue between ether (250 mL) and water (100 mL). The ether was extracted with water (3×25 mL), dried ($MgSO_4$), filtered, and the solvent evaporated in vacuo to leave 23.36 g of crude methyl [3-(2-dioxolanyl)-thiophene-2-ylthio]acetate which was used in the next step without purification.

Theoretical Mass, for $C_{10}H_{12}O_4S_2$:260.0177150; Found: 260.0177150; $^1H$ NMR($CDCl_3$) ω, 3.56(2H, s); 3.71 (3H, s); 4.04 (2H, m); 4.15 (2H, m); 6.08 (1H, s); 7.16 (1H, d, J=6 Hz); 7.37 (1H, d, J=6 Hz).

Step B: Preparation of Methyl (3-Formylthiophene-2-ylthio)acetate

To a solution of methyl [3-(2-dioxolanyl)-thiophene-2-ylthio]acetate (23.36 g) in acetone (100 mL) was added p-toluenesulfonic acid (0.25 g) and the reaction mixture was stirred at room temperature for 1 hour. A saturated aqueous solution of sodium bicarbonate (4 mL) was added with stirring followed by the addition of water (50 mL). After stirring for 10 minutes, the acetone was evaporated in vacuo to leave a gum and water. The gum was dissolved in ether (500 mL) and extracted with water (4×50 mL), dried ($MgSO_4$), filtered and the solvent was evaporated in vacuo to leave 19.77 g of oily methyl (3-formylthiophene-2-ylthio)acetate which was used in the next step without purification.

Step C: Preparation of Methyl thieno[2,3-b]thiophene-2-carboxylate

To a solution of methyl (3-formylthiophene-2-ylthio)acetate (19.31 g, 91 mmol) in methanol (150 mL) was added 1,5-diazabicyclo[4.3.0]non-5-ene (DBN) (1 mL, 1 g, 8.05 mmol) and the stirred reaction flask was immediately immersed in an ice-water bath. Stirring was continued for 30 minutes and the mixture was filtered to give a tacky solid product which was washed with a little cold ($-20°$ C.) methanol. The solvent was evaporated in vacuo from the mother liquor and the residue was partitioned between ether and aqueous sodium bicarbonate. The water layer was washed with ether twice, and the combined ether extracts were dried (MgSO$_4$), filtered, and the solvent evaporated in vacuo to give an oil which solidified when triturated with a little cold ($-20°$ C.) methanol. This was combined with the original solid product to give a total of 14.55 g of methyl thieno-[2,3-b]thiophene-2-carboxylate, m.p. 101°–105° C. Recrystallization from methanol gave product with m.p. 106°–107° C.

Anal. Calc'd for C$_8$H$_6$O$_2$S$_2$: C, 48.47; H, 3.05. Found: C, 48.80; H, 3.32.

Step D: Preparation of 2-Hydroxymethylthieno[2,3-b]-thiophene

A solution of methyl thieno[2,3-b]thiophene-2-carboxylate (19.8 g, 0.1 mol) in dry ether (750 mL) was added at a rapid drip rate (1 hour, 45 minutes) to a suspension of lithium aluminum hydride (7.59 g, 0.2 mol) in ether (500 mL) cooled in an ice-water bath. During the addition, precipitated material on the inside of the flask was kept suspended in the reaction medium. After the addition was complete stirring was continued at room temperature for 3 hours. The reaction mixture was cooled in an ice-water bath and there was added in succession, slowly, dropwise with vigorous stirring: water (7.6 ml); 20% aqueous NaOH (22.8 mL); water (7.6 mL); water (4 mL); 20% sodium hydroxide (12 mL); water (4 ml). Vigorous stirring was continued until a granular precipitate was obtained. The ether was decanted and the solids were washed by decantation three times with ether. The combined ether fractions were dried (MgSO$_4$), filtered, and evaporated in vacuo to leave 16.33 g of white, solid 2-hydroxymethyl-thieno[2,3-b]-thiophene, m.p. 85°–87° C. Recrystallization from hexane gave material with m.p. 86°–87° C.

Anal. Calc'd for C$_7$H$_6$OS$_2$: C, 49.38; H, 3.55 Found: C, 49.69; H, 3.72.

Step E. Preparation of Thieno[2,3-b]thiophene-2-carboxaldehyde

2-Hydroxymethylthieno[2,3-b]thiophene (16.33 g, 95.9 mmol) dissolved in methylene chloride (165 mL) is added all at once to a stirred suspension of pyridinium chlorochromate (31.0 g, 143.9 mmols) in methylene chloride (172 mL) and stirring was continued at ambient temperature for 2 hours. The mixture was diluted with ether (288 mL) and the supernatant was decanted. The solids were washed three times by trituration with ether. The combined ether extracts were filtered through a 60×150 mm silica gel (230–400 mesh) column under pressure and followed with 3 portions of ether. The ether phase of the combined filtrates was evaporated in vacuo to give 13.86 g, of thieno[2,3-b]thiophene-2-carboxaldehyde, m.p. 43°–45° C. Sublimation at 108° C. bath temperature and 0.5 mm pressure gave 13.10 g, m.p. 47°–48° C.

Anal. Calc'd for C$_7$H$_4$OS$_2$: C, 49.98; H, 2.40. Found: C, 50.25; H, 2.45.

Step F: Preparation of 2-(2-dioxolanyl)thieno[2,3-b]thiophene p-Toluenesulfonic acid (150 mg) is added to a stirred two phase mixture of thieno[2,3-b]thiophene-2-carboxaldehyde (8.06 g, 47.91 mmol); ethylene glycol (21.4 g, 345 mmols); methyl orthoformate (30.51 g, 287.5 mmols); and toluene (50 mL). The reaction quickly became homogeneous and stirring was continued with the reaction immersed in an oil bath at 45° to 50° C. A gentle vacuum was applied through an air condenser every 30 to 60 minutes for 5 hours and the reaction was stirred at 45°–50° C. overnight. The reaction was cooled in an ice-water bath and pyridine (0.5 mL) was added. The solvent and volatiles were evaporated in vacuo. The remaining oil was dissolved in ether (250 mL) and extracted with a saturated solution of sodium bicarbonate (2×50 mL), then water (4×50 mL), dried (MgSO$_4$), filtered, and the volumn of ether reduced to about 75 mL in vacuo as the product began to crystallize. The crystals were collected and washed with a little 40% ether in hexane giving 4.08 g of white, solid 2-(2-dioxolanyl)-thieno-[2,3-b]thiophene, m.p. 92°–93° C. The ether from the mother liquors was further reduced in volumn and then allowed to crystallize, to give another 0.76 g of pure product, m.p. 96°–97° C. Both fractions were homogeneous by tlc, and were combined (4.84g) for use in the next step.

Anal. Calc'd for C$_9$H$_8$O$_2$S$_2$: C, 50.92; H, 3.80. Found: C, 51.26; H, 3.93.

Note: This reaction proceeds through the intermediate thieno[2,3-b]thiophene-2-carboxaldehyde dimethyl acetal which was not isolated.

Step G: Preparation of 5-(2-Dioxolanyl)thieno[2,3-b]thiophene-2-sulfonamide

To a cooled mixture of 2-(2-dioxolanyl)-thieno[2,3-b]thiophene (2.12 g, 10 mmol) in dry THF (20 mL) in a nitrogen atmosphere was added butyl lithium (4.4 mL of a 2.3M solution in hexane; 10 mmols) dropwise by syringe over a period of 30 minutes with magnetic stirring. Stirring was continued at $-75°$ C. for 30 minutes. A rapid stream of dry gaseous SO$_2$ was directed at the surface of the stirred mixture at $-75°$ C. The internal reaction temperature rose to $-40°$ C. then cooled to $-75°$ C. again. The SO$_2$ stream was continued for 30 minutes then the reaction was allowed to warm to 10° C. while stirring using the SO$_2$ stream. The excess SO$_2$ and solvent were then evaporated in vacuo to leave 7.09 g of lithium sulfonic acid salt. The salt was dissolved in a saturated solution of sodium bicarbonate (15 mL) and cooled in an ice-water bath. N-chlorosuccinimide (2.00 g, 15 mmol) was added in small portions over a 15 minute period. The reaction was stirred in an ice-water bath for 1 hour, and was then extracted with chloroform three times. The combined extracts were dried (MgSO$_4$), filtered, and the solvent was removed in vacuo to leave 2.73 g of sulfonyl chloride. This intermediate was dissolved in acetone (5 mL) and added dropwise over 30 minutes to an ice cold concentrated ammonium hydroxide solution (15 mL), which was then stirred at ice bath temperature for 1.5 hours. The acetone and ammonia were removed in vacuo leaving a suspension of crystalline product in water. The crystals were collected, washed with water, and dried in a vacuum oven at room temperature with a slow stream of air through the oven to give 1.76 g of crude crystalline 5-(2-dioxolanyl)thieno[2,3-b]thiophene-2-sulfonamide. Recrystallization from nitromethane (Aldrich-Gold label) gave 1.43 g product, which partially melted at 220° C., resolidified and melted >320° C.

$^1$H NMR, (DMSO-d$_6$), ω 3.98; (2H, m); 4.06 (2H, m); 6.09 (1H, s); 7.50 (1H, s); 7.73 (2H, s).

Anal. Calc'd for C$_9$H$_9$NO$_4$S$_3$: 37.10; H, 3.11; N, 4.81. Found: 37.42; H, 3.05; N, 4.92.

Step H: Preparation of 5-Formylthieno[2,3-b]thiophene-2-sulfonamide 5-(2-Dioxolanyl)thieno[2,3-b]thiophene-2-sulfonamide (2.59 g, 8.89 mmol) was suspended in acetone and p-toluenesulfonic acid (2.50 g, 13.1 mmol) was added. The mixture was stirred at room temperature for one hour at which time a solution was obtained. Water (2.0 mL) was added and stirring continued for 3 hours. A saturated solution of sodium bicarbonate (30 mL) was added dropwise, followed by the slow addition of water (40 mL). The resulting solution or mixture was seeded with a few crystals of product and the acetone was evaporated in vacuo. The crystals were collected, washed with water and dried in vacuo to give 2.10 g of 5-formylthieno[2,3-b]thiophene-2-sulfonamide, m.p. 188°–189° C. This product was used in the next step without further purification.

Anal. Calc'd for $C_7H_5NO_3S_3$: C, 34.00; H, 2.04; N, 5.66. Found: C, 34.18; H, 1.99; N, 5.58.

Step I: Preparation of 5-Isobutyliminomethylthieno-[2,3-b]thiophene-2-sulfonamide 5-Formylthieno[2,3-b]thiophene-2-sulfonamide (1.48 g, 6 mmol) was suspended in methanol (15 mL) and isobutylamine (4.2 mL, 3.07 g, 42 mmols) was added all at once. After a solution was obtained, methanolic HCl (1.8 mL of a 6.70 molar solution of HCl in methanol) was added rapidly. The resulting mixture was stoppered and heated to near reflux for 2 to 5 minutes and then allowed to stand at room temperature until the product crystallized. After cooling, the crystals were collected and washed with a little cold (−20° C.) methanol. The crystals were dried in vacuo to give 1.31 g of 5-N-isobutyliminomethylthieno[2,3-b]thiophene-2-sulfonamide, m.p. 204°–206° C. (dec).

Step J: Preparation of 5-Isobutylaminomethylthieno-[2,3-b]thiophene-2-sulfonamide 5-N-Isobutyliminomethylthieno[2,3-b]thiophene-2-sulfonamide (1.30 g, 4.30 mmols) was dissolved in methanol (15 mL) and THF (15 mL) and the solution was cooled in an ice-water bath. To this cooled solution was added sodium borohydride 95 mg (2.5 mmol) three times at 30 minute intervals with 30 minutes of stirring after the last addition. Water was added and the mixture was stirred at room temperature for 1 hour. The methanol and THF were evaporated in vacuo and the resulting crystalline mass was collected and washed twice with water by trituration. The product was dried in vacuo at room temperature to give 1.20 g of 5-isobutylaminomethylthieno[2,3-b]thiophene-2-sulfonamide which was used in the next step without further purification.

Step K: Preparation of 5-Isobutylaminomethylthieno-[2,3-b]thiophene-2-sulfonamide hydrochloride 5-Isobutylaminomethylthieno[2,3-b]thiophene-2-sulfonamide (0.95 g, 3.12 mols) is dissolved in 58 mL of absolute ethanol and filtered. Ethanolic HCl (0.80 mL of a 5.10 M solution of HCl in ethanol; 4.08 mmols) was added and the reaction swirled and then allowed to stand. The resulting crystals are collected, washed with absolute ethanol twice, then washed with ether twice and dried in vacuo to give 0.98 g of 5-isobutylaminomethylthieno[2,3-b]thiophene-2-sulfonamide hydrochloride, m.p. 251°–252° C.

Anal. Calc'd for $C_{11}H_{17}ClN_2O_2S_3$: C, 38.75; H, 8.22; N, 5.03. Found: C, 39.01; H, 8.28; N, 5.07.

EXAMPLE 2

Step A: Preparation of 5-t-Butylaminomethylthieno-[2,3-b]thiophene-2-sulfonamide t-Butylamine (0.736 mL, 0.512 g, 7 mmol) was added to a suspension of 5-formylthieno[2,3-b]-thiophene (0.247 g, 1 mmol) in methanol (2.5 mL). The mixture was warmed gently to obtain solution. Methanolic HCl (0.30 mL of a 6.70 M solution of HCl in methanol; 2 mmol) was added and the mixture was warmed with stirring to 50° C. and stirred at room temperature for 1 hour. THF (2.5 mL) was added to effect solution and the mixture was cooled in an ice-water bath. Sodium borohydride (0.183 g, 4.84 mmols) was added all at once with stirring and stirring was continued for 30 minutes with tlc (10% methanol in chloroform saturated with ammonia and water-silica gel) showed the reaction to be complete. The product was worked up by adding water (50 mL) and 1N HCl to pH 9. The crystalline product was collected and washed with water and dried in vacuo to give 0.25 g of 5-t-butylaminomethylthieno[2,3-b]-thiophene-2-sulfonamide, m.p. 208°–209° C. (dec).

Step B: Preparation of 5-t-Butylaminomethylthieno-[2,3-b]thiophene-2-sulfonamide hydrochloride Substituting 5-t-butylaminomethylthieno-[2,3-b]thiophene-2-sulfonamide for the isobutyl compound in Example 1, Step K, gave the title compound, m.p. 292°–293° C. (dec); (placed in bath at 285° C.).

Anal. Calc'd for $C_{11}H_{17}ClN_2O_2S_3$: C, 38.75; H, 5.03; N, 8.22. Found: C, 39.12; H, 5.28; N, 8.40.

EXAMPLE 3

5-Methylaminomethylthieno[2,3-b]thiophene-2-sulfonamide hydrochloride

Substituting methylamine (as a titrated methylamine solution in methanol) for isobutylamine in Example 1, Step I, and then proceeding substantially as described in Steps J and K gave the title compound after recrystallization from methanol, m.p. 263°–264° C.(dec).

Anal. Calc'd for $C_8H_{11}ClN_2O_2S_3$: C, 32.15; H, 3.37; N, 9.37. Found: C, 32.30; H, 3.49; N, 9.27.

EXAMPLE 4

5-(4-Hydroxybutylaminomethyl)thieno[2,3-b]thiophene-2-sulfonamide hydrochloride

Employing the procedures substantially as described in Example 1, Step I, but replacing the isobutylamine with 4-hydroxybutylamine and proceeding as described through Steps J and K gave the title compound, m.p. 200°–202° C. (dec).

Anal. Calc'd for $C_{11}H_{17}ClN_2O_3S_3$: C, 37.02; H, 4.80; N, 7.85. Found: C, 36.99; H, 4.89; N, 7.87.

EXAMPLE 5

5-(2-Hydroxyethylaminomethyl)thieno[2,3-b]thiophene-2-sulfonamide hydrochloride Substituting 2-hydroxyethylamine for t-butylamine in Step A of Example 2 and proceeding through Step B gave the title compound, m.p. 209°–210° C.

Anal. Calc'd for $C_9H_{13}ClN_2O_3S_3$: C, 32.87; H, 3.98; N, 8.52. Found: C, 32.70; H, 4.11; N, 8.89.

EXAMPLE 6

5-(1,2-Dihydroxy-3-propylaminomethyl)thieno[2,3-b]-thiophene-2-sulfonamide hydrochloride 1,2-Dihydroxy-3-propylamine was substituted for isobutylamine in Step I of Example 1 followed by Steps J and K with the following modification in Step J: upon addition of water and evaporating the organic solvent in vacuo a small amount of precipitate was obtained which was filtered off. The pH of the clear resulting solution was adjusted to 8.5 with diluted aqueous sodium hydroxide solution and nearly all of the water was evaporated in vacuo. The resulting gum was extracted by shaking and decanting with ethyl acetate ten times or until no more U.V. positive material was extracted. The combined ethyl acetate extracts were dried (MgSO$_4$), filtered and the solvent evaporated leaving the desired amine. The hydrochloride salt was made in accordance with Example 1, Step K to give the title compound, m.p. 184°–186° C. (dec).

Anal. Calc'd for $C_{10}H_{15}ClN_2O_4S_3$.0.15 mole EtOH: C, 34.47; H, 4.38; N, 7.66. Found: C, 34.30; H, 4.33; N, 7.97.

EXAMPLE 7

5-(Cyclopropylmethylaminomethyl)thieno[2,3-b]-thiophene-2-sulfonamide hydrochloride Substituting cyclopropylmethylamine for isobutylamine in Step I of Example 1 and proceeding through Step K (but with the addition of exactly one equivalent of HCl as ethanolic HCl in Step K) gave the title compound, m.p. 264°–265° C. (dec).

Anal. Calc'd for $C_{11}H_{15}ClN_2O_2S_3$: C, 38.99; H, 4.46; N, 8.27. Found: C, 39.04; H, 4.52; N, 8.29.

EXAMPLE 8

5-[(N-Methoxyethyl-N-methoxyethoxyethyl)aminomethyl]-thieno[2,3-b]thiophene-2-sulfonamide

Step A: Preparation of 5-[(N-Methoxyethyl-N-methoxyethoxyethyl)aminomethyl]thieno[2,3-b]thiophene-2-sulfonamide N-Methoxyethyl-N-methoxyethoxyethylamine (36.0 g., 203 mmoles) was dissolved in methanol (112 mL). To this solution was added methanolic HCl(5.554M in MeOH) (28.2 mL), 157 mmoles) and this was stirred for 10 minutes. 5-Formylthieno[2,3-b]-thiophene-2-sulfonamide(8.80 g., 35.6 mmoles) was added and the mixture was stirred for 24 hours. 4°A sieves (23.7 g.) were added and the mixture under Argon was stirred for an additional 6 days. Sodium cyanoborohydride (4.47 g. 71.2 mmoles) was added and this was stirred under Argon for 48 hours. Methanol (250 mL) and THF (250 mL.) were added to dissolve all the product. The solution was then filtered through a pad of celite and all solvent was evaporated in vacuo. H$_2$O (100 mL) was added followed by the slow addition of conc. HCl (100 mL). The liquid was decanted and filtered from solid. The acid solution of product was saved. More product was recovered from insoluble material by dissolving the insoluble material in THF (100 mL). Conc. HCl (25 mL) was added and the solution heated to reflux three times in a 15 minute interval. 100 ml of water was added and the THF evaporated off. A clear solution was decanted from the insoluble material. To the combined acidic water solution of product was added conc. NH$_4$OH until pH was 8.5 (125 mL), and this was then extracted five times over MgSO$_4$. The solvent was filtered and evaporated in vacuo to leave 10.16 g of crude product, which was chromatographed on 2.4 kg. of silica gel, eluting with 3% methanol in chloroform to give 7.7 g of highly pure 5-[(N-methoxyethyl-N-methoxyethoxyethyl)-aminomethyl]thieno[2,3-b]thiophene-2-sulfonamide.

Step B: Preparation of 5-[(N-Methoxyethyl-N-methoxyethoxyethyl)aminomethyl]thieno[2,3-b]thiophene-2-sulfonamide hydrochloride 5-[(N-Methoxyethyl-N-methoxyethoxyethyl)aminomethyl]-thieno[2,3-b]thiophene-2-sulfonamide (6.42 g., 15.71 mmole) from Step A was dissolved in i-propanol (550 mL) filtered and methanolic HCl (5.54M) (3.00 mL; 16.6 mmoles) was added. The resulting mixture was swirled, allowed to stand for 15 minutes, and was boiled down to 200 mL and seeded. On cooling most of the product oiled out. A crust of crystals formed and this was broken up by trituration to provide 5.64 g of pure 5-[(N-Methoxyethyl-N-methoxyethoxyethyl)aminomethyl]-thieno[2,3-b]thiophene-2-sulfonamide hydrochloride, mp 147°–148° C.

Anal. Calc'd for $C_{15}H_{25}ClN_2O_5S_3$: C, 40.48; H, 5.66; N, 6.30 Found: C, 40.52; H, 5.28; N, 6.30.

EXAMPLE 9

5-(2-Methoxyethylaminomethyl)thieno[2,3-b]thiophene-2-sulfonamide hydrochloride Substituting 2-methoxyethylamine for isobutylamine in Step I of Example 1 and proceeding through Step K gave the title compound, m.p. 223°–224° C.

Anal. Calc'd for $C_{10}H_{15}ClN_2O_3S_3$: C, 35.03; H, 4.41; N, 8.17 Found: C, 35.04; H, 4.46; N, 8.03

Employing the procedures described in the foregoing the compounds depicted in the following table are prepared from the appropriate starting materials.

TABLE

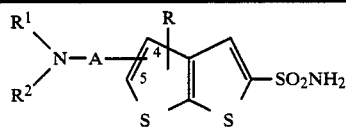

| A | R$^1$ | R$^2$ | R | melting or decomposition point (°C.) |
|---|---|---|---|---|
| 5-CH$_2$— | H | CH$_3$O(CH$_2$)$_3$— | H | 230–232 (HCl) |

TABLE-continued $$\begin{array}{c} R^1 \\ \diagdown \\ R^2 \end{array} N-A- \overset{R}{\underset{S}{\underbrace{\phantom{XXX}}_{4}}}\phantom{X}\overset{\phantom{X}}{\underset{S}{\underbrace{\phantom{XXX}}}}-SO_2NH_2$$

| A | R$^1$ | R$^2$ | R | melting or decomposition point (°C.) |
|---|---|---|---|---|
| 5-CH$_2$— | H | CH$_3$O(CH$_2$)$_2$O(CH$_2$)$_3$— | H | (154–155) + 244–245 (HCl) |
| 5-CH$_2$— | —CH$_2$CH$_2$—O—CH$_2$CH$_2$—* | | H | 264–265 (HCl) |
| 5-CH$_2$— | H | CF$_3$CH$_2$— | H | 230–232 (HCl) |
| 5-CH$_2$— | H | CH$_3$S(CH$_2$)$_2$— | H | 224–225 (HCl) |
| 5-CH$_2$— | H | f—(CH$_2$)$_2$— | H | 221–222 (HCl) |
| 5-CH$_2$— | CH$_3$O(CH$_2$)$_2$— | CH$_3$O(CH$_2$)$_2$—* | H | (155–157) + 190–192 (HCl) |
| 5-CH$_2$— | H | $\underset{CH_3S(CH_2)_2-}{\overset{O}{\underset{\|}{\|}}}$ | H | 110–112 (HCl) |
| 5-CH$_2$— | —CH$_2$CH$_2$SCH$_2$CH$_2$— | | H | 248 250 (HCl) |
| 5-CH$_2$— | CH$_3$— | CH$_3$— | H— | |
| 4-CH$_2$— | CH$_3$— | CH$_3$— | H— | |
| 5-CH$_2$— | C$_2$H$_5$— | C$_6$H$_5$CH$_2$— | H— | |
| 5-CH$_2$— | H— | C$_2$H$_5$— | 4-CH$_3$— | |
| 5-CH$_2$CH$_2$— | CH$_3$— | CH$_3$— | H— | |
| 5-CH$_2$CH$_2$— | i-C$_4$H$_9$— | H— | 4-CH$_3$— | |
| 4-CH$_2$— | CH$_3$— | CH$_3$OCH$_2$CH$_2$— | H— | |
| 5-CH$_2$— | H— | (CH$_3$)$_2$N—CH$_2$— | H— | |

*Intermediate iminium compound was reduced with sodium cyanoborohydride.
+ Compound scinters or melts at parenthetical temperature, resolidifies and melts or decomposes at higher temperature.

EXAMPLE 10

| EXAMPLE 10 | | |
|---|---|---|
| 5 isobutylaminomethylthieno-[2,3-b]thiophene-2-sulfonamide hydrochloride | 1 mg | 15 mg |
| Monobasic sodium phosphate 2H$_2$O | 9.38 mg | 6.10 mg |
| Dibasic sodium phosphate .12H$_2$O | 28.48 mg | 16.80 mg |
| Benzalkonium chloride | 0.10 mg | 0.10 mg |
| Water for injection q.s. ad. | 1.0 ml | 1.0 ml |

The novel compound, phosphate buffer salts, and benzalkonium chloride are added to and dissolved in water. The pH of the composition is adjusted to 5.4–7.4 and diluted to volume. The composition is rendered sterile by ionizing radiation.

EXAMPLE 11

| EXAMPLE 11 | |
|---|---|
| 5-t-Butylaminomethylthieno-[2,3-b]thiophene-2-sulfonamide | 5 mg |
| petrolatum q.s. ad. | 1 gram |

The compound and the petroleum are aseptically combined.

EXAMPLE 12

| EXAMPLE 12 | |
|---|---|
| 5-Methylaminomethylthieno-[2,3-b]thiophene-2-sulfonamide hydrochloride | 1 mg |
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. 5-[N-Methoxyethyl-N-methoxyethoxyethyl)amino-methyl]thieno[2,3-b]thiophene-2-sulfonamide.

2. An ophthalmological formulation for the treatment of ocular hypertension and glaucoma comprising an ophthalmologically acceptable carrier and an effective ocular antihypertensive amount of the compound of claim 1.

3. A method of treating ocular hypertension and glaucoma which comprises the topical ocular administration to a patient in need of such treatment of an effective ocular antihypertensive amount of the compound of claim 1.

* * * * *